United States Patent [19]

Haworth et al.

[11] Patent Number: 4,502,630
[45] Date of Patent: Mar. 5, 1985

[54] VAPOR-DISPENSING DEVICE

[75] Inventors: Brian D. Haworth, Farnborough, England; Edward J. Malek, Racine County, Wis.

[73] Assignee: S. C. Johnson & Son, Inc., Racine, Wis.

[21] Appl. No.: 503,958

[22] Filed: Jun. 13, 1983

[51] Int. Cl.³ .............................................. A61L 9/12
[52] U.S. Cl. .................................................... 239/34
[58] Field of Search ............................ 239/34, 53-57; 220/334, 339, 265, 266; 206/0.5

[56] References Cited

U.S. PATENT DOCUMENTS 4,130,245 12/1978 Bryson ................................... 239/34
4,161,284 7/1979 Rattan ................................ 239/56 X Primary Examiner—Andres Kashnikow

[57] ABSTRACT

A device for dispensing air-treating vapors having two support members between which is a flexible, generally flat dispensing pouch. The pouch has an inner storage container of an air-treating composition which is burstable by applying sandwiching pressure on the dispensing pouch through the support members to release the composition for dispensing. The support members have facing, substantially parallel apertured support surfaces which engage the pouch and are relatively movable between a first spacing in which the storage container is protected from bursting and a second spacing allowing bursting of the pouch. A spacer interconnecting one pair of aligned edges of the support members may be removed to allow bursting, and the aligned edges preferably thereafter reconnected at a closer spacing to hold the released composition in contact with much of the inner surface of the dispensing pouch.

13 Claims, 5 Drawing Figures

U.S. Patent    Mar. 5, 1985    4,502,630
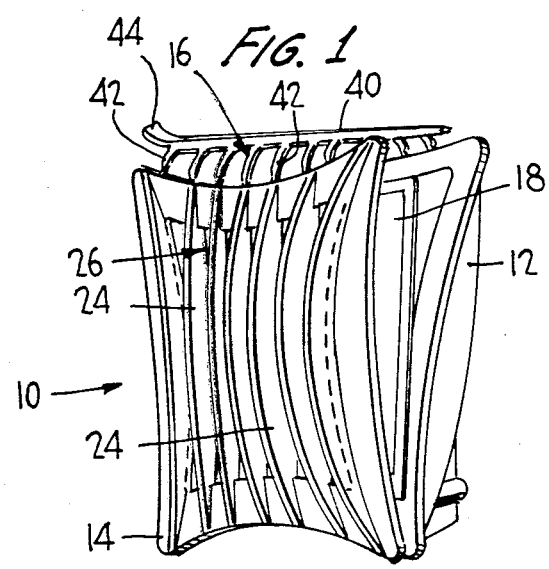
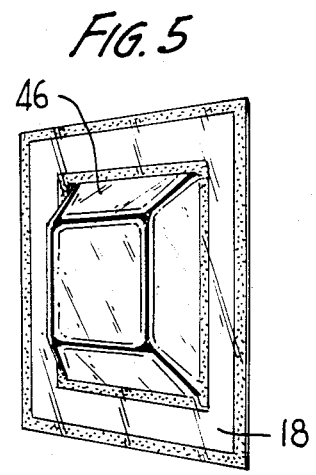
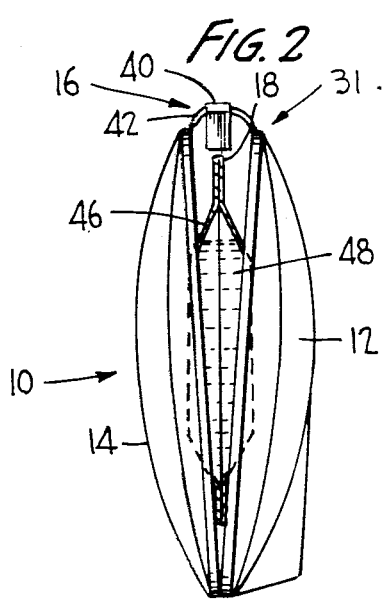
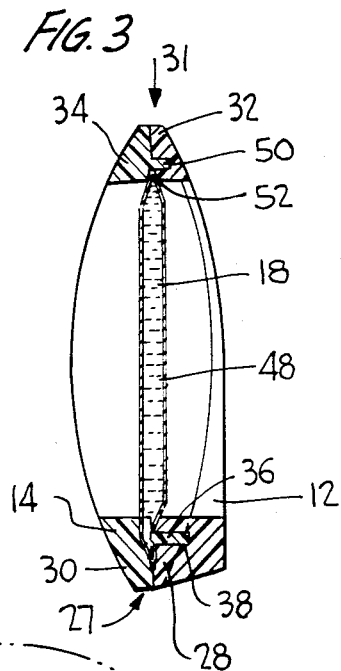
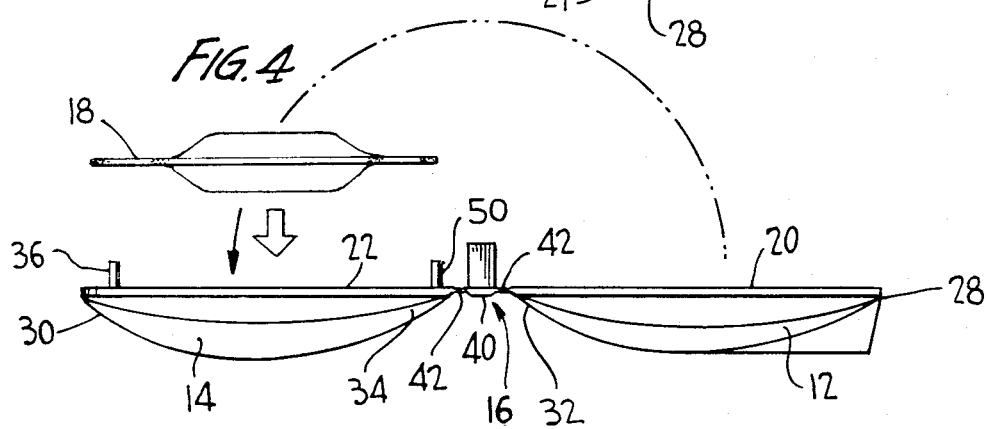

VAPOR-DISPENSING DEVICE

FIELD OF THE INVENTION

This invention relates to devices for providing a continuous release of air-treating vapors. More specifically, this invention relates to devices for releasing vapors to the atmosphere at a substantially constant rate.

BACKGROUND OF THE INVENTION

A great variety of devices have been developed to dispense air-treating vapors. A number of the recent inventions in this field include a liquid air-treating composition in an enclosure all or part of which is formed of a polymeric material (such as film) through which the air-treating composition can migrate to be released as a vapor at an outer surface. Use of such a permeable polymeric material controls the dispensing of air-treating vapors and tends to eliminate great variations in the rate of dispensing over the life of the product. Such products are considered advantageous in this regard when compared with the many air-treating products for which the rate of vapor release drops dramatically over the life of the product.

Products of the type having a sheet of permeable polymeric material to control the emission of air-treating vapors may be in a variety of forms. In some, the polymeric sheet covers a cylindrical container, while in others the liquid air-treating material is trapped between the permeable sheet and an impermeable plastic sheet. In still others, the permeable polymeric material forms a flexible pouch containing the air-treating liquid, which, prior to activation, is contained within an air-impermeable breakable container such as a glass vial, an impermeable plastic inner pouch, or the like. This invention is related primarily to products using a permeable pouch or bag to control the emission of air-treating vapors. An example of this type of pouch is disclosed in PCT Publication No. WO 82/02700.

For products having such pouches, it is often desirable for a number of reasons to contain and support the permeable pouch in some manner. For example, the user may wish to avoid contact with the air-treating material which occurs when the pouch is touched. Also, contact of the pouch with such finished surfaces, such as furniture, can harm the finish in some cases. Another important reason to contain and support such pouches is related to the rate of vapor dispensing, as will be discussed further in the following paragraphs.

When flexible permeable plastic bags containing liquid or other flowable material are used for vapor dispensing, the rate of dispensing will vary as the area of contact between the contained liquid and the inner surface of its enclosure varies. Pooling of the liquid at the enclosure bottom, as can often occur depending on the orientation of the enclosure, can substantially reduce the dispensing rate. The rate of vapor-dispensing is significantly increased and will remain very steady over the life of the product when the liquid is in contact with all or nearly all of the inner surface of the enclosure.

This problem is specifically pointed out in U.S. Pat. No. 4,130,245 (Bryson), entitled "Liquid Dispensing Package." See, for example, column 1, lines 23–40. The Bryson patent attempts to solve this problem by dividing the flexible plastic bag into a plurality of small chambers such that the liquid will not pool primarily in one location. While this approach may have some advantages for certain types of packages, it cannot readily be used when the flexible dispensing bag is of the type having a single chamber which encloses a smaller burstable inner storage container filled with an air-treating liquid composition to be released into the flexible dispensing bag upon bursting, as is shown in FIG. 1 of PCT Publication No. WO 82/02700.

The Bryson invention is not applicable to the problem of uneven dispensing for flexible dispensing bags of the type shown herein. There is a need for a device to improve the distribution of a liquid air-treating composition within a flexible enclosure of the type having a single dispensing chamber, in order that the full advantages of dispensing by permeation through polymeric materials can be realized.

There is a need for a simple, inexpensive device for supporting a flexible plastic pouch for dispensing air-treating vapors from a contained liquid. The device should serve to: isolate the pouch away from finished surfaces; eliminate the need for human contact with such pouch; allow good air circulation against the pouch; allow each visual inspection to determine when the pouch is empty; hold the contained liquid in good contact with a large portion of the inner surface of the permeable pouch to improve dispensing characteristics; and also protect the burstable impermeable inner container (such as a pouch within the permeable pouch) from premature, unintentional bursting. Given the number of functions such device would serve, low cost and simplicity are not easily achieved.

There is a need for such a device which may be readily adaptable for use as a so-called "small spaces" vapor dispenser, that is, a small, inexpensive vapor-dispensing device of a type suitable for placement in drawers, closets, small rooms, and the like. This invention provides all of the aforementioned advantages in a simple, inexpensive device useful as a "small spaces" vapor dispenser. This invention may also be used for larger vapor-dispensing devices, such as those which may be placed on a countertop or the like.

DESCRIPTION OF THE INVENTION

The present invention is a device for dispensing air-treating vapors from a flexible, generally flat dispenser pouch containing a liquid air-treating composition. The device of this invention overcomes problems of prior art devices while providing the other desirable qualities and advantages mentioned above.

The device of this invention includes two support members constructed and arranged such that a flexible, generally flat dispensing pouch can be supported between them. The support members have facing, substantially parallel support surfaces (one surface on each of the support members) and are relatively movable to adjust the spacing of such surfaces. At least one, and preferably both, of the support members are grates; that is, they are apertured to allow access of the atmosphere to the outer surfaces of the flexible dispenser pouch. The grates have members spaced closely together or otherwise have pouch contact surfaces providing adequate engagement with the flexible pouch. The flexible pouch is sandwiched between the support surfaces and can be squeezed by sandwiching force exerted through the support members.

The flexible dispenser pouch includes an inner storage container filled with a flowable, vaporizable air-treating composition, preferably a liquid. Such inner storage container is burstable by the aforementioned sandwiching pressure to release the composition into the flexible dispenser pouch for dispensing by permeation through the surface of the pouch.

The support members have first and second pairs of aligned edges along opposite ends of the support surfaces. The support members are interconnected along both such pairs of aligned edges. The spacing of the support surfaces and the interaction of such surfaces with the flexible dispenser pouch are determined by the nature of the connecting means.

A spacer member interconnects the support members along one of the pairs of aligned edges. The spacer maintains the support surfaces at a large enough spacing such that bursting of the inner storage container is prevented while the spacer remains in place. However, the spacer is made to be torn away or otherwise removed such that the support members can be squeezed together. Such squeezing causes application of sandwiching pressure on the inner storage container, through the support surfaces and the flexible dispenser pouch, to burst the inner storage container.

Along the aligned edges having the spacer, there are secondary connecting means to hold the support members in a closer relationship after the spacer is torn away. This allows the support surfaces to firmly engage the pouch and spread the liquid into near complete contact with the inner surfaces of the flexible dispenser pouch. Thus, the dispensing characteristics of the pouch are improved.

The spacer member is preferably a strip connected to each of the support members by frangible connector means, which are preferably several breakable strands integrally formed with the strip and the support members. Indeed the entire construction, except the pouch, is preferably integrally formed of plastic, such as by molding.

The spacer may function as a hinge between the support members to facilitate insertion of the flexible pouch during assembly of the device. The pouch may be inserted when the support members are spread wide apart. Then the support members are swung together around the hinge, and the aligned ends of the support members which are remote from the hinge are connected by snap fitments formed thereon or other suitable means. The hinge then begins its function as a spacer to protect the inner storage container from unintentional bursting.

OBJECTS OF THE INVENTION

It is an object of this invention to provide a device for dispensing air-treating vapors overcoming problems of the prior art.

Another object of this invention is to provide an improved air-treating vapor dispenser of the type including a liquid air-treating composition within a flexible enclosure.

Another object of this invention is to provide a simple, inexpensive dispenser for air-treating vapors providing favorable dispensing characteristics of more complex and expensive devices.

Still another object of this invention is to provide a dispenser for air-treating vapors of the type including a burstable container which includes a simple device protecting the container from unintentional bursting.

Yet another object of this invention is to provide a dispenser for air-treating vapors of the type described which minimizes variations in the rate of vapor-dispensing over the life of the product.

These and other important objects of the invention will be apparent from the following description of preferred embodiments of the invention and from the accompanying drawings wherein:

BRIEF DESCRIPTION OF THE DRAWINGS

FIG. 1 is a perspective view of the device of this invention.

FIG. 2 is a side elevation of FIG. 1.

FIG. 3 is a sectional view showing the device in activated position.

FIG. 4 is another side elevation of the device of FIG. 1 but in open unassembled condition.

FIG. 5 is a perspective view of the flexible dispenser pouch inside the device.

DETAILED DESCRIPTION OF PREFERRED EMBODIMENTS

The drawings illustrate a preferred vapor-dispensing device 10 in accordance with this invention. Vapor-dispensing device 10 includes first and second support members 12 and 14, respectively, a spacer member 16 interconnecting support members 12 and 14, and a flexible dispenser pouch 18 sandwiched between support members 12 and 14.

Support members 12 and 14 have substantially parallel support surfaces 20 and 22, respectively, which are grates made of a number of generally parallel bars 24 with apertures 26 therebetween. Support surfaces 12 and 14 also have a first pair 27 of aligned edges, including edges 28 and 30, and an opposite pair 31 of aligned edges, including edges 32 and 34. The support surfaces 20 and 22 engage the opposite sides of pouch 18 at a spacing which is determined by the nature of the connections along the first and second pairs 27 and 31 of aligned edges.

As illustrated in FIG. 3, male snap elements 36 on second support member 14 and female snap elements 38 on first support member 12 form snap fitment means along the first pair 27 of aligned edges to interconnect support members 12 and 14. As illustrated in FIGS. 1 and 2, spacer member 16 interconnects the second pair 31 of aligned edges and maintains them at a first spacing such that pouch 18 is not substantially squeezed between support surfaces 20 and 22. These connections along the first and second pairs 27 and 31 of aligned edges are in use prior to activation of air-treating device 10.

Spacer member 16 has a tear strip 40 which is connected to support members 12 and 14 by a number of breakable strands 42 which are integrally formed with strip 40 and support members 12 and 14. Strip 40 has a tab portion 44 which may be gripped in one hand, while the main portion of device 10 is held in the other, and torn away to allow support members 12 and 14 to be readily squeezed together. Such squeezing action serves to activate the pouch for dispensing of air-treating vapors.

As shown in FIG. 5, vapor-dispensing pouch 18 has an inner storage pouch 46 which holds a liquid air-treating composition 48 before the device is activated. Inner storage pouch 46 is itself a flexible plastic pouch, formed of material which is impermeable to liquid composition 48. Vapor-dispensing pouch 18 is made of a permeable plastic material through which liquid composition 48 can migrate to be released at its outer surface as a vapor. Suitable materials for pouch 18 and pouch 46 are known in the art and do not form part of this invention. However, attention is directed to the above-mentioned PCT International Publication and to U.S. Pat. Nos. 3,951,622 and 4,248,380, which discuss materials and liquid compositions which are suitable for use in this invention. Particular attention is directed to a commonly assigned copending patent application of Edward J. Malek, Ser. No. 488,287, filed Apr. 25, 1983, entitled "Method for Forming a Burstable Pouch", now abandoned.

When it is desired to activate vapor-dispensing device 10, spacer member 16 is torn away, as already described, and the user squeezes first and second support members 14 and 16 together until inner storage pouch 46 bursts, releasing air-treating liquid 48 into the portion of vapor-dispensing pouch 18 which is outside pouch 46. Support members 12 and 14 can be squeezed together until liquid 48 is distributed across vapor-dispensing pouch 18 to give complete or nearly complete contact of liquid 48 with the lateral walls of pouch 18, as illustrated in FIG. 3.

After support members 12 and 14 are squeezed together, they are held together by virtue of secondary snap fitments which include male snap elements 50 on second support member 14 and female snap elements 52 on first support member 12. While prior to activation spacer member 16 holds support surfaces 20 and 22 at a first spacing such that inner pouch 46 cannot readily be burst, after actuation snap fitments 50 and 52 secure support members 12 and 14 together such that support surfaces 20 and 22 are at a second, much closer, spacing. In such second spacing, pouch 18 is supported by support surfaces 20 and 22 to distribute liquid 48 for contact with a large portion of the inner surface of pouch 18.

Spacer member 16 functions as a hinge during the assembly of device 10. As illustrated in FIG. 4, support members 12 and 14 are, prior to assembly, hinged open such that pouch 18 can be loaded onto support surface 22. Thereafter, support members 12 and 14 are rotated relative one to the other around spacer member 16 until the first pair 27 of aligned edges are connected as previously described.

Support members 12 and 14, spacer member 16, and all of the snap fitments previously described are integrally molded of plastic materials. Preferred materials include high density polyethylene and polypropylene, but a variety of suitable materials will be apparent to those skilled in the art.

Vapor-dispensing pouch 18 is preferably translucent and, most preferably, both pouch 18 and pouch 46 are translucent. This enables the user to determine when the liquid composition has been fully dispensed. Varying degrees of translucency are possible; indeed, the pouches can be transparent or nearly transparent. It is only desirable that the user be able to see the contents of such pouches.

While in the foregoing specification, this invention has been described in relation to certain preferred embodiments and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A device for dispensing air-treating vapors comprising:

two support members having facing, substantially parallel support surfaces and having first and second pairs of aligned edges along opposite ends of the support surfaces, at least one of such support surfaces being a grate;

a flexible, generally flat dispenser sandwiched between the support surfaces and having an inner storage container of vaporizable air-treating composition which is burstable by sandwiching pressure exerted through the support surfaces to release the composition for dispensing;

means along said first pair of aligned edges interconnecting said support members; and a spacer member interconnecting said support members along said second pair of aligned edges and maintaining said support surfaces at a first spacing such that the inner storage container cannot be burst, said spacer member being removable to allow application of sandwiching pressure on said inner storage container through said support surfaces and said flexible dispenser to burst said storage container.

2. The device of claim 1 further including secondary means along said second pair of aligned edges to interconnect said support members in a second spacing after removal of a spacer member, said second spacing being closer than said first spacing.

3. The device of claim 1 wherein both of said support surfaces are grates.

4. The device of claim 1 wherein the spacer member is a strip connected to each of the support members by frangible connector means.

5. The device of claim 4 wherein the frangible connector means comprise a multiplicity of breakable strands integrally formed with the strip and the support members.

6. The device of claim 1 wherein the spacer member is a hinge between the two support members.

7. The device of claim 6 wherein the means interconnecting the first pair of aligned edges are snap fitments, such that the flexible dispenser can be loaded into the device when the support members are hinged open and the devices thereafter snapped closed along said first pair of aligned edges with the hinge then assuming its function as spacer.

8. The device of claim 1 wherein the support members, spacer member, and all of the interconnecting means are integrally formed of plastic.

9. The device of claim 8 further including secondary means along said second pair of aligned edges to interconnect said support members in a second spacing after removal of a spacer member, said second spacing being closer than said first spacing.

10. The device of claim 9 wherein the spacer member is a hinge between the two support members.

11. The device of claim 10 wherein the means interconnecting the first pair of aligned edges are snap fitments, such that the flexible dispenser can be loaded into the device when the support members are hinged open and the devices thereafter snapped closed along said first pair of aligned edges with the hinge then assuming its function as spacer.

12. The device of claim 11 wherein the spacer member is a strip connected to each of the support members by frangible connector means.

13. The device of claim 12 wherein the frangible connector means comprises a multiplicity of breakable strands integrally formed with the strip and the support members.

* * * * *